United States Patent [19]
Grasselli et al.

[11] 3,932,551
[45] Jan. 13, 1976

[54] PROCESS FOR THE PREPARATION OF DIOLEFINS FROM OLEFINS

[75] Inventors: Robert K. Grasselli, Chagrin Falls; Dev. D. Suresh, Warrensville Heights; James L. Callahan, Bedford Heights, all of Ohio

[73] Assignee: The Standard Oil Company, Cleveland, Ohio

[22] Filed: Oct. 12, 1973

[21] Appl. No.: 405,940

[52] U.S. Cl............. 260/680 E; 252/462; 252/468; 252/469; 252/470
[51] Int. Cl.².......................................... C07C 5/48
[58] Field of Search ................................ 260/680 E

[56] References Cited
UNITED STATES PATENTS

| | | | |
|---|---|---|---|
| 3,414,631 | 12/1968 | Grasselli et al. | 260/680 E |
| 3,642,930 | 2/1972 | Grasselli et al. | 260/680 E |
| 3,764,632 | 10/1973 | Takenaka et al. | 260/680 E |
| 3,801,670 | 4/1974 | Shiraishi et al. | 260/680 E |
| 3,825,502 | 7/1974 | Takenaka et al. | 252/456 |

*Primary Examiner*—Paul M. Coughlan, Jr.
*Attorney, Agent, or Firm*—Herbert D. Knudsen

[57] ABSTRACT

Catalysts containing molybdenum, bismuth, iron and nickel, cobalt, magnesium, zinc, cadmium, manganese, calcium or mixture thereof are promoted by chromium, tellurium, germanium, tungsten, manganese, thorium, niobium, praseodymin, cerium, lanthanum, zinc or mixture thereof to give highly desirable catalysts for the oxidative dehydrogenation of olefins of 4 to about 10 carbon atoms.

7 Claims, No Drawings

PROCESS FOR THE PREPARATION OF DIOLEFINS FROM OLEFINS

BACKGROUND OF THE INVENTION

The oxidative dehydrogenation of olefins is known, see for example U.S. pat. Nos. 3,414,631 and 3,642,930. The process of the present invention is conducted within the parameters of the art, but uses a different catalyst.

SUMMARY OF THE INVENTION

It has been discovered in the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising using as the catalyst a catalyst wherein the atomic ratios are described by the empirical formula $$A_a C_c D_d Fe_e Bi_f Mo_g O_x$$

wherein
A is chromium, tellurium, germanium, tungsten, manganese, thorium, niobium, praseodymium, cerium, lanthanum, zinc or mixture thereof;
C is an alkali metal, alkaline earth metal, Tl, In, Ag, Cu, Sn, Sb, rare earth metal or mixture thereof;
D is nickel, cobalt, magnesium, zinc, cadmium, manganese, calcium or mixture thereof; A is not the same as D;
and wherein
$a$ is greater than zero to about 4;
$c$ is 0 to about 4;
$d$ is 0.1 to about 20;
$e$ and $f$ are 0.01 to 12;
$g$ is 10 to 15; and
$x$ is the number of oxygens required by the valence states of the other elements present.

The process of the invention gives highly desirable yields of the diolefin product, long catalyst life is realized and large quantities of product are produced in a given period of time.

The present invention is the use of a different catalyst in the known oxidative dehydrogenation of olefins. The central aspect of this invention is the catalyst.

The catalyst is suitably any catalyst containing the combination of elements delimited by the formula above. Preferred are catalysts that contain nickel, cobalt, magnesium or mixture thereof and those catalysts that contain potassium, or cesium. Catalysts of the invention that contain germanium, chromium, manganese, niobium, lanthanum, zinc or mixture thereof are especially preferred because of the high per pass conversions to useful diolefin products.

the catalysts of the invention are conveniently prepared by any of the methods associated with the similar oxidation catalysts in the art. One of ordinary skill in the art knows a number of preparations from related catalysts that contain many common elements. Among methods of combining the elements of the catalyst are the coprecipitation of soluble salts from a solution and the mixing of salts or oxides of the various compounds. After the elements of the catalyst are combined, the preparation of the catalyst is completed by calcination of the catalyst at an elevated temperature. Temperatures between about 200° and about 600°C. are most suitable.

Specific preparations of catalysts of the invention are shown in the Specific Embodiments. These preparations give preferred catalysts of the invention.

The catalysts of the invention may be used as pure catalytic material or they may be used in a supported form. Suitable support materials include silica, alumina, titania, zirconia, boron phosphate and the like. The use of catalysts supported on silica is preferred.

The oxidative dehydrogenation reaction of the invention is known. The invention is operated within the parameters of the art processes even though a different catalyst is employed.

Broadly, the reaction of the invention reacts an olefin of 4–10 carbon atoms with molecular oxygen, normally added as air, in the presence of a catalyst. The ratio of molecular oxygen is about 0.2 to about 8 moles of oxygen per mole of olefin. The reactants could be diluted with a diluent such as steam, carbon dioxide or the like.

Preferred reactants in the present invention are the n-butenes which are converted to butadiene by the process of the invention. Also preferred is the reaction of isoamylene to obtain isoprene.

The reaction is normally conducted at temperatures between about 200° and about 600°C., with temperatures of about 300° to about 500°C. being preferred. The reactants can be passed over the catalyst at an apparent contact time as low as a fraction of a second to 20 seconds or more. The reaction can be conducted in a fluid-bed or fixed-bed reactor at atmospheric, superatmospheric or subatmospheric pressure. Using these techniques, the reaction of the present invention gives highly desirable yields of diolefins from the corresponding olefin. When used in the oxydehydrogenation reaction, the catalysts are remarkably stable, and large amounts of product in a given time are produced.

SPECIFIC EMBODIMENTS

EXAMPLES 1–9 —

Oxidative dehydrogenation of butene-1

A reactor was constructed from a 0.8 cm. diameter stainless steel tube having an inlet for reactants and an outlet for products. The reactor had a reaction zone which could be charged with 2.5 c.c. of catalyst.

Various catalysts of the invention were prepared as described below. All catalysts contained 80% active ingredients and 20% silica.

EXAMPLE 1

$Cr_{0.5}K_{0.1}Ni_{2.5}Co_{4.5}Fe_3BiMo_{12}O_x$

In 100 ml. of water, 63.56 g. of ammonium heptamolybdate, $(NH_4)_6Mo_7O_{24}.4H_2O$, was dissolved and 51.66 g. of Nalco 40% silica sol was added with stirring and heating. To this slurry was added 1.50 g of $CrO_3$.

Separately, 36.36 g. of ferric nitrate, $Fe(NO_3)_3.9H_3O$, was heated and dissolved in 10 c.c. of water. Then 14.55 g. $Bi(NO_3)_3. 5H_2O$, 39.29 g of $Co(NO_3)_2.6H_2O$, 21.81 g. of $Ni(NO_3)_2.6H_2O$ and 3.03 g. of a 10% solution of $KNO_3$ was dissolved in the solution. The nitrate solution was slowly added to the slurry containing the molybdenum. The mixture was heated and stirred until it began to thicken. The solid was dried in an oven at 120°C. with occasional stirring. The final catalyst was calcined in air at 550°C. for 16 hours.

EXAMPLE 2

$Te_{0.5}K_{0.1}Ni_{2.5}Co_{4.5}Fe_3BiMo_{12}O_x$

The catalyst was prepared in the same manner as shown in Example 1, except that 4.04 g. TeCl4 was substituted for the CrO₃.

EXAMPLE 3

$Ge_{0.5}K_{0.1}Ni_{2.5}Co_{4.5}Fe_3BiMo_{12}O_x$

The catalyst was prepared in the same manner as Example 1, except that 1.57 g. of GeO₂ was substituted for the CrD₃.

EXAMPLE 4

$W_{0.5}K_{0.1}Ni_{2.5}Co_{4.5}Fe_3BiMo_{12}O_x$

The catalyst was prepared as described in Example 1, except that 4.04 g. of $(NH_4)_6W_7O_{24} \cdot 6H_2O$ was substituted for the CrO₃.

EXAMPLE 5

$Mn_{0.5}K_{0.1}Ni_{2.5}Co_{4.5}Fe_3BiMo_{12}O_x$

The catalyst was prepared as described in Example 1, except that 5.37 g. of a 50% solution of manganese nitrate was substituted for the CrO₃.

EXAMPLE 6

$Th_{0.5}K_{0.1}Ni_{2.5}Co_{4.5}Fe_3BiMo_{12}O_x$

The catalyst was prepared as shown in Example 1, except that 8.28 g. of $Th(NO_3)_4 \cdot 4H_2O$ was substituted for the CrO₃.

EXAMPLE 7

$Nb_{0.5}K_{0.1}Ni_{2.5}Co_{4.5}Fe_3BiMo_{12}O_x$

In 50 c.c. of warm water, 31.8 g. of ammonium heptamolybdate was dissolved. To this solution was added 2.0 g. of NbCl₅ slurried with water, 26.5 g. of Nalco 40% silica sol and a mixture of 10.9 g. of nickel nitrate and 19.7 g. cobalt nitrate.

Separately, a solution of 18.2 g. ferric nitrate, 7.2 g. of bismuth nitrate and 0.19 g. KOH as a 45% solution was prepared, and the solution was slowly added to the molybdenum slurry. The remainder of the preparation was the same as Example 1.

EXAMPLE 8

$Pr_{0.5}K_{0.1}Ni_{2.5}Co_{4.5}Fe_3BiMo_{12}O_x$

The catalyst was prepared as shown in Example 1, except that 2.60 g. of PrO₂ was substituted for the CrO₃.

EXAMPLE 9

$Ce_{0.5}K_{0.1}Ni_{2.5}Co_{4.5}Fe_3BiMo_{12}O_x$

The catalyst was prepared as described in Example 1, except that 8.22 g. of $(NH_4)_2Ce(NO_3)_6$ was substituted for the CrO₃.

The catalyst samples were ground and screened to give a 20 to 35 mesh fraction that was charged to the 2.5 c.c. reaction zone of the reactor. A butene-1/air/steam feed of a molar ratio of 1/11/4 was fed over the catalyst at a temperature of 350°C. for an apparent contact time of 1 second.

The results of these experiments are stated in the following terms:

$$\% \text{ conversion} = \frac{\text{olefin reacted} \times 100}{\text{olefin fed}}$$

$$\% \text{ selectivity} = \frac{\text{product recovered} \times 100}{\text{olefin reacted}}$$

$$\% \text{ single pass yield} = \frac{\text{product recovered} \times 100}{\text{olefin fed}}$$

The results of these experiments are given in Table I. Isomerization of butene-1 is not computed as olefin reacted.

TABLE I

Oxidative Dehydrogenation of Butene-1 To Butadiene With $X_{0.5}K_{0.1}Ni_{2.5}Co_{4.5}Fe_3BiMo_{12}O_x$

| Example | Catalyst X= | Conversion | Selectivity to Butadiene | Single Pass Yield of Butadiene |
|---|---|---|---|---|
| 1 | Cr | 100 | 98 | 97.7 |
| 2* | Te | 98.8 | 98 | 97.3 |
| 3 | Ge | 98.8 | 98 | 96.8 |
| 4 | W | 98.6 | 96 | 95.7 |
| 5* | Mn | 98.4 | 97 | 95.2 |
| 6* | Th | 98.4 | 97 | 95.2 |
| 7 | Nb | 97.6 | 95 | 92.6 |
| 8* | Pr | 97.5 | 94 | 92.1 |
| 9* | Ce | 100 | 92 | 92.1 |

*no steam in feed

EXAMPLES 10–17 — Oxidative dehydrogenation of butene-1 with germanium containing catalysts Various catalysts containing germanium were prepared as follows:

EXAMPLE 10

The catalyst was prepared the same as the catalyst of Example 1 except that no potassium was added and 1.57 g. GeO₂ was substituted for CrO₃.

EXAMPLE 11

The catalyst was prepared as shown in Example 10 except that the normal amount of potassium was added, and 61.04 g. of nickel nitrate was used instead of the nickel and cobalt.

EXAMPLE 12

The catalyst was prepared as shown in Example 11 except that 61.12 g. of cobalt nitrate was substituted for the nickel nitrate.

EXAMPLE 13

The catalyst was prepared as shown in Example 11 except that 72.83 g. of ammonium heptamolybdate and 3.03 g. of a 45% KOH solution were used.

EXAMPLE 14

The catalyst was prepared as shown in Example 11, except that 53.85 g. of $Mg(NO_3)_2 \cdot 6H_2O$ was added instead of the nickel and cotalt, and 3.22 g. of GeCl₄ was used in place of GeO₂.

EXAMPLE 15

The catalyst was prepared as shown in Example 11 except that magnesium nitrate was substituted for the nickel nitrate, and GeCl₄ was used as shown in Example 14.

EXAMPLE 16

The catalyst was prepared as shown in Example 11 except that manganese nitrate in the form of a 50% solution was substituted for the cobalt.

EXAMPLE 17

The catalyst was prepared as shown in Example 11 except that 2.72 g. of $GeCl_4$ was used for the germanium, 21.48 g. of a 50% solution of manganese nitrate replaced the nickel and 3.03 g. of a 45% solution of KOH were employed.

The catalysts were tested as shown in Examples 1–9. The results are shown in Table II.

TABLE II

Germanium-Containing Catalysts to Convert Butene-1 to Butadiene

| Example | Catalyst | Conversion | Results, % Selectivity | Single Pass Yield |
|---|---|---|---|---|
| 10 | $Ge_{0.5}Ni_{2.5}Co_{4.5}Fe_3BiMo_{12}O_x$ | 98.8 | 91 | 90.4 |
| 11 | $Ge_{0.5}K_{0.1}Ni_7Fe_3BiMo_{12}O_x$ | 99.9 | 94 | 94.3 |
| 12 | $Ge_{0.5}K_{0.1}Co_7Fe_3BiMo_{12}O_x$ | 87.4 | 99 | 86.8 |
| 13 | $Ge_{0.5}K_{0.8}Ni_{2.5}Co_{4.5}Fe_3BiMo_{13.75}O_x$ | 100.0 | 99 | 99.2 |
| 14 | $Ge_{0.5}K_{0.1}Mg_7Fe_3BiMo_{12}O_x$ | 98.7 | 98 | 96.8 |
| 15 | $Ge_{0.5}K_{0.1}Mg_{2.5}Co_{4.5}Fe_3BiMo_{12}O_x$ | 99.4 | 99 | 98.1 |
| 16 | $Ge_{0.5}K_{0.1}Ni_{2.5}Mn_{4.5}Fe_3BiMo_{12}O_x$ | 96.9 | 97 | 93.7 |
| 17 | $Ge_{0.4}K_{0.8}Mn_2Co_5Fe_3BiMo_{12}O_x$ | 55.2 | 99 | 54.6 |

EXAMPLE 18

Two promoters in thallium containing catalyst

A catalyst of the formula 80% $Ge_{0.5}Cr_{1.5}Tl_{0.1}Ni_2Co_3Fe_{0.5}BiMo_{12}O_x$ and 20% $SiO_2$ was prepared in the same manner as described for the examples above and used in the oxydehydrogenation of butene-1 using a butene-1/air ratio of 1/11, a temperature of 350°C. and an apparent contact time of one second. The conversion of the butene-1 was 89.6%, the selectivity was 98% and the single pass yield was 88.1%.

EXAMPLE 19

Cesium containing catalyst

A catalyst of the formula 80% $Mn_{0.5}Cs_{0.1}Ni_{2.5}Co_{4.5}Fe_3BiMo_{12}O_x$ and 20% $SiO_2$ was prepared as shown in Example 5 except that 0.59 g. cesium nitrate, $CsNO_3$, was substituted for the potassium compound. Using the feed and conditions of Example 18, butene-1 was 100% converted to products, the selectivity to butadiene was 99% and the single pass yield was 98.6%.

EXAMPLES 20–28

Oxydehydrogenation of butene-2.

Catalysts prepared in the examples above were used in the oxydehydrogenation of butene-2 to butadiene. Using the reactor, catalyst volumes of the examples above and an apparent contact time of 1 second, a mixture of 57.5% trans and 42.5% cis butene-2 was reacted. The ratio of butene-2/air was 1/11. The results of these experiments are given in Table III.

TABLE III

Oxydehydrogenation of Butene-2 to Butadiene

| Example | Catalyst | Reaction Temp., °C | Conversion | Results, % Selectivity | Single Pass Yield |
|---|---|---|---|---|---|
| 20 | $Ce_{0.5}(K_{0.1}Ni_{2.5}Co_{4.5}Fe_3BiMo_{12}O_x)$ | 350 | 95.4 | 93 | 88.3 |
| 21 | $Nb_{0.5}($ " $)$ | " | 93.0 | 95 | 88.1 |
| 22 | $Pr_{0.5}($ " $)$ | 375 | 97.7 | 89 | 87.3 |
| 23 | $Mn_{0.5}($ " $)$ | 385 | 95.1 | 93 | 88.9 |
| 24 | $Cr_{0.5}($ " $)$ | " | 95.6 | 95 | 90.9 |
| 25 | $Ge_{0.5}($ " $)$ | " | 84.4 | 95 | 80.5 |
| 26 | $W_{0.5}($ " $)$ | " | 85.0 | 95 | 80.3 |
| 27 | $Th_{0.5}($ " $)$ | 400 | 90.5 | 92 | 82.7 |
| 28* | $Ge_{0.5}K_{0.8}Ni_{2.5}Co_{4.5}Fe_3BiMo_{13.75}O_x$ | 375 | 95.7 | 90 | 86.5 |

*4 sec. contact time

EXAMPLES 29–38

Operation at high air-to-olefin ratios

Catalysts of the invention prepared as described above were used to oxydehydrogenate a mixture of butene-2 in the same manner as shown for Examples 20–28, except that the butene-2/air ratio was 1/31. The reaction temperature was 350°C., and the apparent contact time was one second. The results of these experiments are shown in Table IV. The lanthanum catalyst of Example 37 was prepared by substituting 6.22 g. of $La(NO_3)_3 \cdot 5H_2O$ for the $CrO_3$ in the catalyst of Example 1. The zinc catalyst of Example 38 was prepared by substituting 4.46 g. of $Zn(NO_3)_2 \cdot 6H_2O$ for the $CrO_3$ of Example 1.

TABLE IV

Oxydehydrogenation of Butene-2 with Catalyst of $X_{0.5}K_{0.1}Ni_{2.5}Co_{4.5}Fe_3BiMo_{12}O_x$

| Example | Catalyst, X= | Conversion | Selectivity | Results, % Single Pass Yield |
|---|---|---|---|---|
| 29 | Mn | 100 | 97 | 96.8 |
| 30 | Cr | 96.6 | 96 | 92.5 |
| 31[1.] | Nb | 100 | 93 | 92.8 |
| 32 | Ce | 100 | 89 | 88.9 |
| 33[1.] | Ce | 100 | 91 | 90.9 |
| 34 | Ge | 81.5 | 98 | 80.0 |

TABLE IV-continued

Oxydehydrogenation of Butene-2 with
Catalyst of $X_{0.5}K_{0.1}Ni_{2.5}Co_{4.5}Fe_3BiMo_{12}O_x$

| Example | Catalyst, X= | Conversion | Selectivity | Results, %<br>Single Pass Yield |
|---|---|---|---|---|
| 35[2] | W | 92.9 | 91 | 84.2 |
| 36[2] | Th | 96.7 | 90 | 86.7 |
| 37 | La | 100 | 95 | 95.4 |
| 38 | Zn | 100 | 95 | 94.7 |

[1] Reaction temperature 340°C.
[2] Reaction temperature 385°C.

EXAMPLE 39

High air ratios with different potassium catalyst

A catalyst of 80% $W_{0.5}K_{0.5}Ni_{2.5}Co_{4.5}Fe_3BiMo_{12}O_x$ and 20% $SiO_2$ was prepared as described in Example 9 except that five times the potassium was added. Using the mixture of butene-2 above in a ratio of air-to-butene-2 of 31, an apparent contact time of one second and a temperture of 385°C. this catalyst was tested for the production of butadiene. The conversion of the butene-2 was 96.4%, the selectivity was 91% and the single pass yield was 88.1%.

EXAMPLE 40

Oxydehydrogenation of isoamylene

With the catalyst of Example 13, in a reactor having a reaction zone of 5 c.c., a mixture of equal volumes of 2-methylbutene-1 and 2-methylbutene-2 was oxydehydrogenated to give isoprene. At 400°C. and an apparent contact time of 2 seconds, the conversion of the isoamylene was 85.9%, the selectivity to isoprene was 82% and the single pass yield to isoprene was 70.2%.

EXAMPLE 41

Preparation of isoprene with Cr catalyst

In the same manner shown by Example 40, the catalyst of Example 1 was used to prepare isoprene. The conversion was 86.2%, the selectivity was 70%, and the single pass yield was 60.5%.

We claim:

1. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising
    using as the catalyst a catalyst wherein the atomic ratios are described by the empirical formula
    $Te_a C_c D_d Fe_e Bi_f Mo_g O_x$
    wherein
    C is an alkali metal, alkaline earth metal, Tl, In, Ag, Cu, Sn, Sb, rare earth metal or mixture thereof;
    D is nickel, cobalt, magnesium, zinc, cadmium, manganese, calcium or mixture thereof;
    and wherein
    a is greater than zero to about 4;
    c is 0 to about 4;
    d is 0.1 to about 20;
    e and f are 0.01 to 12;
    g is 10 to 15; and
    x is the number of oxygens required by the valence states of the other elements present.

2. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising
    using as the catalyst a catalyst wherein the atomic ratios are described by the empirical formula
    $Ge_a C_c D_d Fe_e Bi_f Mo_g O_x$
    wherein
    C is an alkali metal, alkaline earth metal, Tl, In, Ag, Cu, Sn, Sb, rare earth metal or mixture thereof;
    D is nickel, cobalt, magnesium, zinc, cadmium, manganese, calcium or mixture thereof;
    and wherein
    a is greater than zero to about 4;
    c is 0 to about 4;
    d is 0.1 to about 20;
    e and f are 0.01 to 12;
    g is 10 to 15; and
    x is the number of oxygens required by the valence states of the other elements present.

3. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising
    using as the catalyst a catalyst wherein the atomic ratios are described by the empirical formula
    $Th_a C_c D_d Fe_e Bi_f Mo_g O_x$
    wherein
    C is an alkali metal, alkaline earth metal, Tl, In, Ag, Cu, Sn, Sb, rare earth metal or mixture thereof;
    D is nickel, cobalt, magnesium, zinc, cadmium, manganese, calcium or mixture thereof;
    and wherein
    a is greater than zero to about 4;
    c is 0 to about 4;
    d is 0.1 to about 20;
    e and f are 0.01 to 12;
    g is 10 to 15; and
    x is the number of oxygens required by the valence states of the other elements present.

4. In the process for the oxidative dehydrogenation of an olefinic hydrocarbon of four to about 10 carbon atoms comprising contacting a mixture of the olefin and molecular oxygen with a catalyst at a temperature of 200° to about 600°C., the improvement comprising
    using as the catalyst a catalyst wherein the atomic ratios are described by the empirical formula
    $Nb_a C_c D_d Fe_e Bi_f Mo_g O_x$
    wherein
    C is an alkali metal, alkaline earth metal, Tl, In, Ag, Cu, Sn, Sb, rare earth metal or mixture thereof;
    D is nickel, cobalt, magnesium, zinc, cadmium, manganese, calcium or mixture thereof;
    and wherein
    a is greater than zero to about 4;
    c is 0 to about 4;

d is 0.1 to about 20;

e and f are 0.01 to 12;

g is 10 to 15; and x is the number of oxygens required by the valence states of the other elements present.

5. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising using as the catalyst a catalyst wherein the atomic ratios are described by the empirical formula

wherein

C is an alkali metal, alkaline earth metal, Tl, In, Ag, Cu, Sn, Sb, rare earth metal or mixture thereof;

D is nickel, cobalt, magnesium, zinc, cadmium, manganese, calcium or mixture thereof;

and wherein a is greater than zero to about 4;

c is greater than zero to about 4;

d is 0.1 to about 20;

e and f are 0.01 to 12;

g is 10 to 15; and x is the number of oxygens required by the valence states of the other elements present.

6. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising using as the catalyst a catalyst wherein the atomic ratios are described by the empirical formula $Ce_a C_c D_d Fe_e Bi_f Mo_g O_x$ wherein C is an alkali metal, alkaline earth metal, Tl, In, Ag, Cu, Sn, Sb, rare earth metal or mixture thereof;

D is nickel, cobalt, magnesium, zinc, cadmium, manganese, calcium or mixture thereof;

and wherein a is greater than zero to about 4;

c is greater than zero to about 4;

d is 0.1 to about 20;

e and f are 0.01 to 12;

g is 10 to 15; and x is the number of oxygens required by the valence states of the other elements present.

7. In the process for the oxidative dehydrogenation of an olefinic hydrocarbon of four to about 10 carbon atoms comprising contacting a mixture of the olefin and molecular oxygen with a catalyst at a temperature of about 200° to about 600°C., the improvement comprising using as the catalyst a catalyst wherein the atomic ratios are described by the empirical formula $La_a C_c D_d Fe_e Bi_f Mo_g O_x$ wherein C is an alkali metal, alkaline earth metal, Tl, In, Ag, Cu, Sn, Sb, rare earth metal or mixture thereof;

D is nickel, cobalt, magnesium, zinc, cadmium, manganese, calcium or mixture thereof;

and wherein a is greater than zero to about 4;

c is greater than zero to about 4;

d is 0.1 to about 20;

e and f are 0.01 to 12;

g is 10 to 15; and x is the number of oxygens required by the valence states of the other elements present.

* * * * *